US012658081B2

(12) United States Patent
Porubanova et al.

(10) Patent No.: US 12,658,081 B2
(45) Date of Patent: Jun. 16, 2026

(54) ADJUSTING FRAME RATE BASED UPON DETECTED CHANGE IN STIMULUS ATTRIBUTE

(71) Applicant: Microsoft Technology Licensing, LLC, Redmond, WA (US)

(72) Inventors: Michaela Porubanova, Seattle, WA (US); Gregory Michael Link, Charlotte, NC (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 18/677,226

(22) Filed: May 29, 2024

(65) Prior Publication Data
US 2025/0372007 A1 Dec. 4, 2025

(51) Int. Cl.
*A61B 5/16* (2006.01)
*G02B 27/01* (2006.01)
*G09G 3/00* (2006.01)
*H04N 13/344* (2018.01)

(52) U.S. Cl.
CPC .............. *G09G 3/001* (2013.01); *A61B 5/161* (2013.01); *A61M 2205/507* (2013.01); *G02B 27/017* (2013.01); *G09G 2320/0247* (2013.01); *G09G 2330/021* (2013.01); *G09G 2340/0435* (2013.01); *H04N 13/344* (2018.05)

(58) Field of Classification Search
CPC .......... G09G 3/001; G09G 2320/0247; G09G 2330/021; G09G 2340/0435; A61M 2205/507; G02B 27/017; H04N 13/344; A61B 5/161
See application file for complete search history.

(56) References Cited

U.S. PATENT DOCUMENTS

| | | | | |
|---|---|---|---|---|
| 9,966,007 B2 * | 5/2018 | Cho | ...................... | G06F 1/1652 |
| 2014/0313236 A1 | 10/2014 | Jang | | |
| 2016/0086574 A1 * | 3/2016 | Buckley | .............. | G09G 3/3413 345/690 |
| 2017/0004766 A1 * | 1/2017 | Cho | ...................... | G06F 1/1652 |
| 2021/0390913 A1 | 12/2021 | Lee | | |
| 2025/0037622 A1 * | 1/2025 | Hwang | .................. | G09G 3/002 |

FOREIGN PATENT DOCUMENTS

| | | | | |
|---|---|---|---|---|
| EP | 3113165 B1 | 3/2021 | | |
| KR | 20160053377 A | * 5/2016 | ............. | G02F 1/353 |

OTHER PUBLICATIONS

Mankowska, Critical Flicker Fusion Frequency: A Narrative Review, Oct. 13, 2021, Medicina 2021, 57, 1096 (Year: 2021).*
Critical Flicker Fusion frequency, A Narrative Review (Year: 2021).*
Extended European Search Report received for EP Application No. 25178074.8, mailed on Jul. 10, 2025, 13 pages.

* cited by examiner

*Primary Examiner* — Douglas Wilson
(74) *Attorney, Agent, or Firm* — Alleman Hall LLP

(57) ABSTRACT

One example provides a head-mounted display (HMD) device comprising a display system, a logic subsystem, and a storage subsystem comprising instructions executable by the logic subsystem. The instructions are executable to project images at a first frame rate using the display system, detect a change in a stimulus attribute of the images that modifies a critical flicker fusion (CFF) threshold of a human eye, and in response, adjust a frame rate of the display system to project the images at a second frame rate.

17 Claims, 11 Drawing Sheets

FIRST, LOWER STIMULUS
ILLUMINANCE 502

SECOND, HIGHER STIMULUS
ILLUMINANCE 504

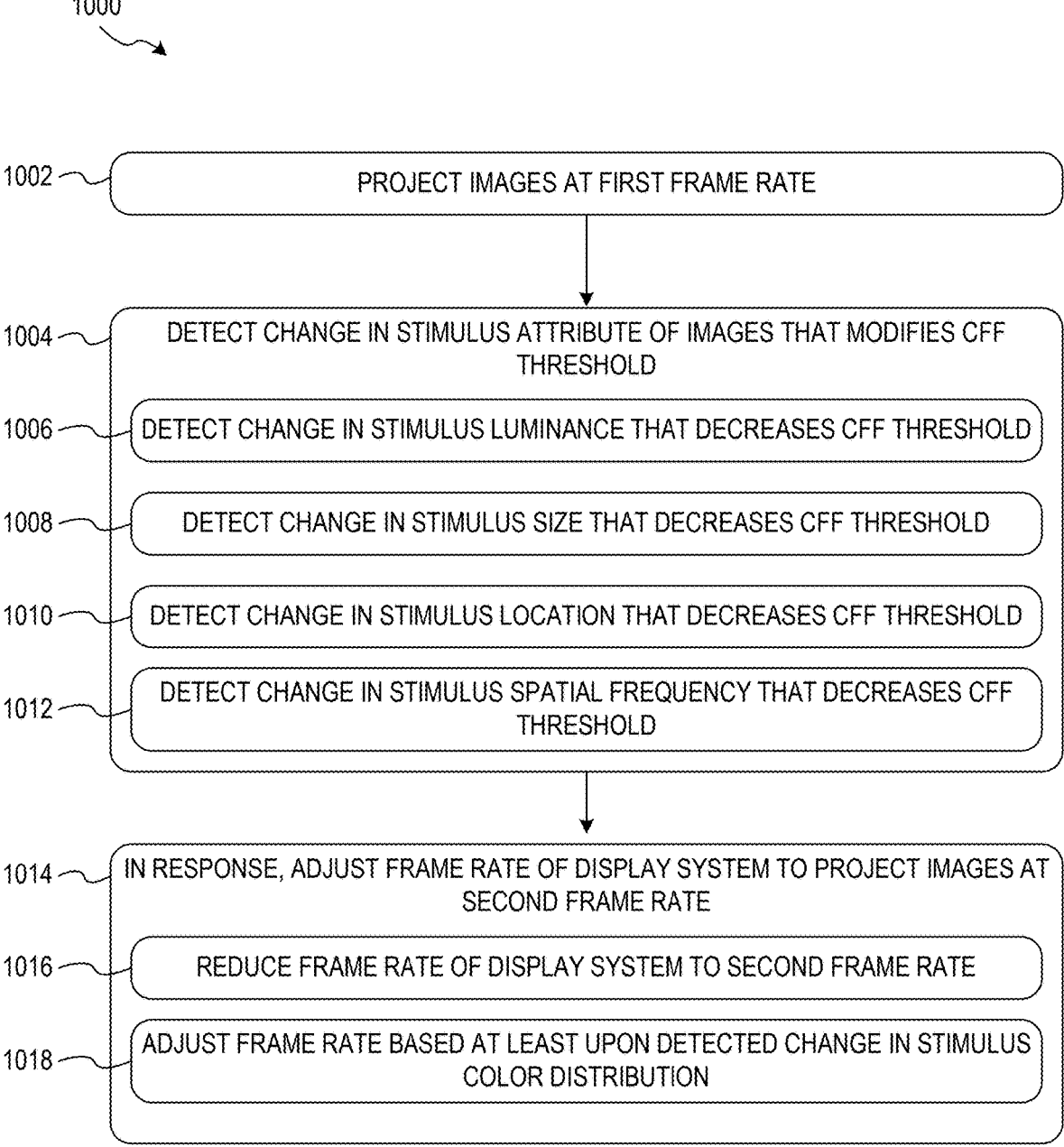

1000

1002 — PROJECT IMAGES AT FIRST FRAME RATE

1004 — DETECT CHANGE IN STIMULUS ATTRIBUTE OF IMAGES THAT MODIFIES CFF THRESHOLD

1006 — DETECT CHANGE IN STIMULUS LUMINANCE THAT DECREASES CFF THRESHOLD

1008 — DETECT CHANGE IN STIMULUS SIZE THAT DECREASES CFF THRESHOLD

1010 — DETECT CHANGE IN STIMULUS LOCATION THAT DECREASES CFF THRESHOLD

1012 — DETECT CHANGE IN STIMULUS SPATIAL FREQUENCY THAT DECREASES CFF THRESHOLD

1014 — IN RESPONSE, ADJUST FRAME RATE OF DISPLAY SYSTEM TO PROJECT IMAGES AT SECOND FRAME RATE

1016 — REDUCE FRAME RATE OF DISPLAY SYSTEM TO SECOND FRAME RATE

1018 — ADJUST FRAME RATE BASED AT LEAST UPON DETECTED CHANGE IN STIMULUS COLOR DISTRIBUTION

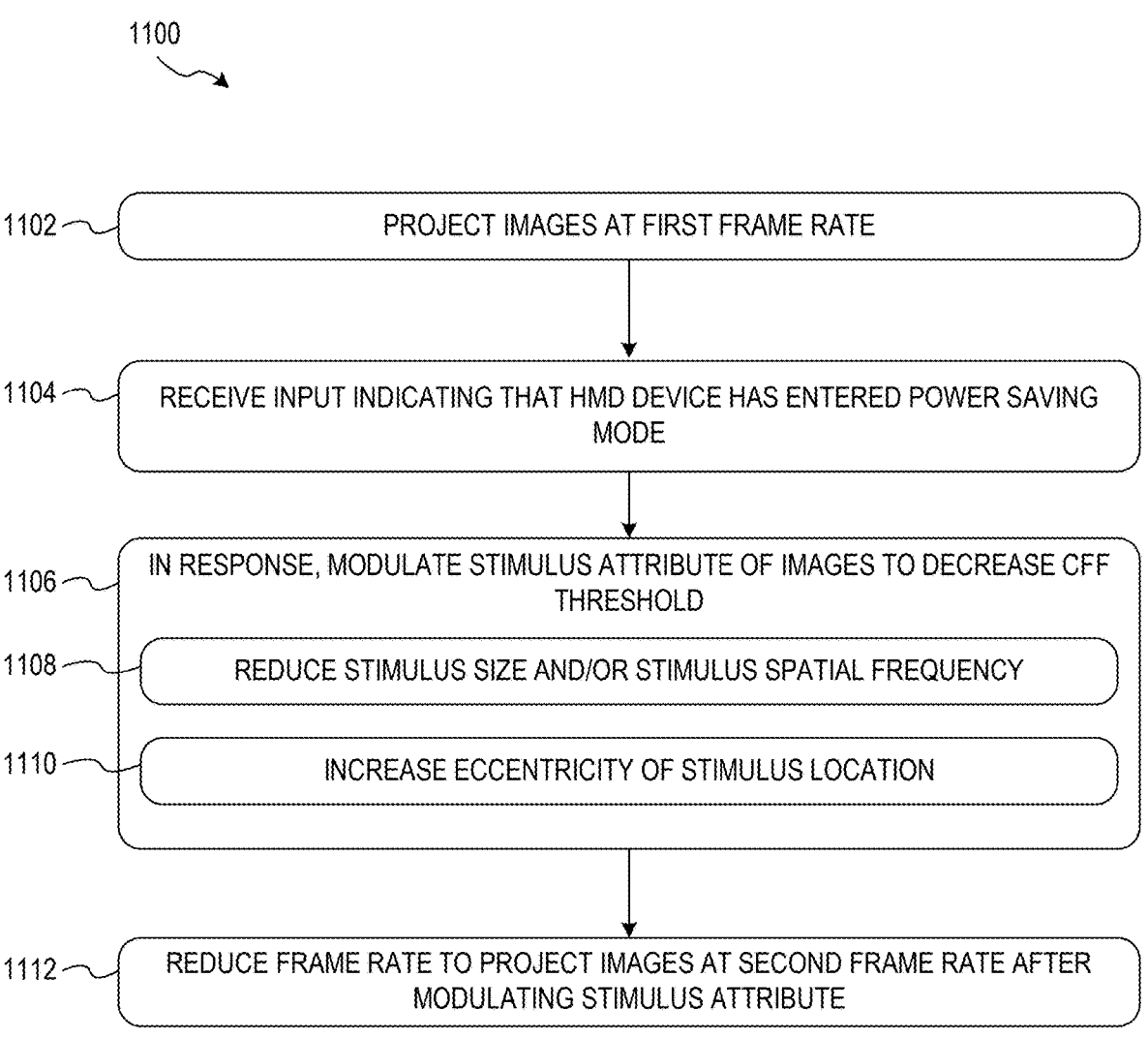

1102 — PROJECT IMAGES AT FIRST FRAME RATE

1104 — RECEIVE INPUT INDICATING THAT HMD DEVICE HAS ENTERED POWER SAVING MODE

1106 — IN RESPONSE, MODULATE STIMULUS ATTRIBUTE OF IMAGES TO DECREASE CFF THRESHOLD

1108 — REDUCE STIMULUS SIZE AND/OR STIMULUS SPATIAL FREQUENCY

1110 — INCREASE ECCENTRICITY OF STIMULUS LOCATION

1112 — REDUCE FRAME RATE TO PROJECT IMAGES AT SECOND FRAME RATE AFTER MODULATING STIMULUS ATTRIBUTE

FIG. 11

ADJUSTING FRAME RATE BASED UPON DETECTED CHANGE IN STIMULUS ATTRIBUTE

BACKGROUND

Near-eye display systems can be utilized in head-mounted display (HMD) devices to present virtual related immersive user experiences. For example, a binocular near-eye display system provides 3D stereo vision for virtual-reality (VR) experiences. When implemented using see-thru optics, the near-eye display system enables mixed-reality (MR) experiences, in which VR elements appear to be visually mixed with a user's natural field of view. Such MR experiences can use 3D holographic images that appear as if they are part of the user's physical environment. This enables realistic and immersive interactions with digital objects.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

One example provides a head-mounted display (HMD) device comprising a display system, a logic subsystem, and a storage subsystem comprising instructions executable by the logic subsystem. The instructions are executable to project images at a first frame rate using the display system, detect a change in a stimulus attribute of the images that modifies a critical flicker fusion (CFF) threshold of a human eye, and in response, adjust a frame rate of the display system to project the images at a second frame rate.

BRIEF DESCRIPTION OF THE DRAWINGS

FIGS. 9A, 9B, and 9C schematically illustrate example changes in a stimulus color distribution.

FIG. 10 depicts a flowchart of an example method for adjusting a frame rate of a display system in response to detecting a change in a stimulus attribute.

FIG. 11 illustrates a flowchart of an example method for modulating a selected stimulus attribute.

DETAILED DESCRIPTION

As mentioned above, an HMD device may include a near-eye display system for VR and/or MR experiences. Such HMD devices project digital content using modulated light to form a temporal sequence of image frames. The temporal sequence of image frames is projected at a frequency referred to as a frame rate. For VR and MR experiences, a frame rate that creates a smooth and realistic illusion of motion and/or depth for the images is desirable. Such a frame rate is reliant on the critical flicker fusion (CFF) threshold of the human eye. The CFF threshold is the threshold frequency at which a flickering light appears the same as a non-flickering light. Therefore, digital images projected at a frame rate that is at or greater than the CFF threshold can create a flicker-free experience (e.g., images appear as continuous visual stimulus, such as a unitary uniform object). This is important in MR/VR devices because it affects the user's perception of the virtual and/or real environments, as well as the user's comfort.

For example, when the frame rate is less than the CFF threshold, the user may perceive flicker in the images which can lead to loss of immersion and/or presence in the VR/MR experience. As a result, such flicker can cause eye strain, fatigue, headaches, and/or motion sickness. Therefore, MR/VR devices generally utilize frame rates that are higher than the CFF threshold to eliminate the flicker in projected images. However, such a high frame rate consumes power at a faster rate than lower frame rates.

Accordingly, examples are disclosed that relate to dynamically adjusting a frame rate based at least upon a change in stimulus attribute of projected images. Briefly, an HMD device projects images at a first frame rate. In response to detecting a change in a stimulus attribute of the images, the HMD device adjusts a frame rate to project the images at a second frame rate. As used herein, the term "stimulus attribute" refers to a characteristic of an image that is discernable by the human eye. Examples of stimulus attributes include a stimulus illuminance, a stimulus size, a stimulus location, a stimulus spatial frequency, and a stimulus color distribution. In some examples, the change in the stimulus attribute is sufficient to modify the CFF threshold of the human eye. As discussed in more detail below, the CFF threshold can vary because of the physiology of the human eye. As such, the HMD device is configured to utilize information on the human visual system to adjust the frame rate based at least upon detecting the change in the stimulus attribute of the images. In such a manner, the HMD device can reduce the frame rate to help both user experience and power consumption of the HMD device.

Figure 1:
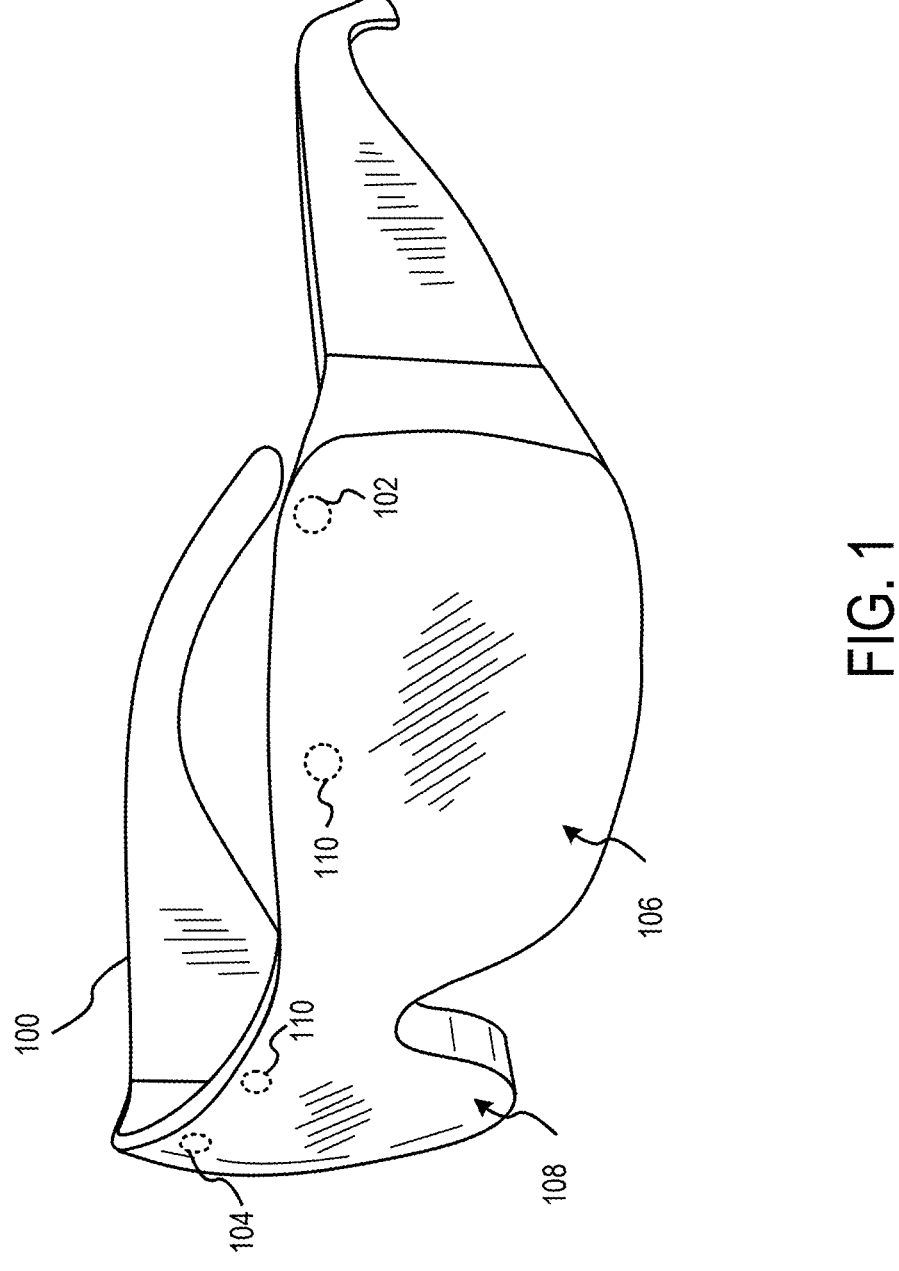
FIG. 1 schematically depicts an example HMD device.

Prior to discussing these examples in detail, FIG. 1 shows an example head-mounted display (HMD) device 100 comprising a binocular display system. The binocular display system comprises a left projector 102 and a right projector 104. Each projector can comprise a scanned beam projector, a microdisplay (such as LCoS, OLED), or other suitable image display mechanism. The binocular display system further comprises a left display 106 and a right display 108 configured to deliver images from the respective projector to the respective eye. Each display can comprise any suitable optics. Example optics include one or more lens(es), waveguide(s), prism(s), and combinations thereof. The images displayed on the left display 106 and the right display 108 can comprise stereoscopic images of virtual objects. In MR applications, the images of virtual objects are overlayed onto a real-world scene such that the virtual objects appear to be present in the real-world scene. In VR applications, the HMD device 100 may instead comprise features (e.g. a display dimmer, such as an electrochromic layer) to hide the real-world scene from the view of a user.

The HMD device 100 also comprises, for each eye, one or more eye-tracking cameras 110 and one or more glint light sources (not depicted in FIG. 1). Each glint light source is configured to direct light (e.g., infrared light) toward the cornea of a user's eye. Image data from each eye-tracking camera 110 is analyzed to determine the location of a glint from each glint light source and a location of the pupil of the eye. The glint and pupil location data may then be used to determine a gaze direction, potentially in combination with suitable anatomical models related, for example, to eye geometry and/or head geometry. In the depicted example, the eye-tracking cameras 110 are schematically depicted as being positioned above the eye. In other examples, the eye-tracking cameras 110 and the glint light sources may be positioned below the eye, to a side of the eye, or in another suitable location. FIG. 1 is illustrative. An HMD device may have another configuration in other examples.

Figure 2:
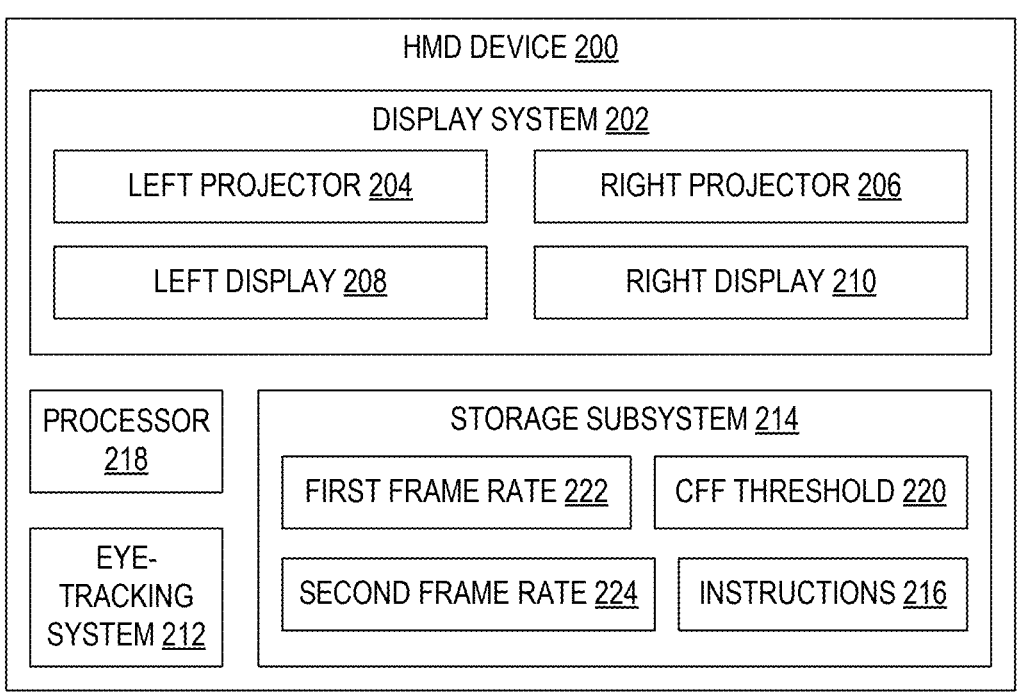
FIG. 2 shows a block diagram of an example HMD device.

FIG. 2 depicts a block diagram of an example HMD device 200. The HMD device 100 is an example implementation of the HMD device 200. The HMD device 200 comprises a display system 202 with a left projector 204 associated with a left eye of a user. The left projector 204 can include any suitable projector technologies, as described above with regard to left projector 102. Similarly, the display system 202 also comprises a right projector 206 associated with a right eye of the user. The display system 202 is configured to project binocular images and/or monocular images. Binocular images are projected using both the left projector 204 and the right projector 206, such as stereoscopic images, for example. Monocular images are projected by either the left projector 204 or the right projector 206. In various examples, the left projector 204 and the right projector 206 can project different monocular images concurrently and/or a suitable combination of binocular images and monocular images. The display system 202 further comprises a left display 208 configured to transmit images from the left projector 204 for viewing. The left display 208 can be any suitable display technology, including the examples disclosed with the left display 106. Likewise, the display system 202 also comprises a right display 210.

The HMD device 200 further includes an eye-tracking system 212 configured to determine a gaze direction of the left eye and/or the right eye of the user. The eye-tracking system 212 can utilize any suitable eye-tracking techniques, including the examples described with the eye-tracking system of the HMD device 100.

The HMD device 200 additionally comprises a storage subsystem 214 having instructions 216 that are executable by a processor 218. The instructions 216 are executable to control various operations of the HMD device 200. Specifically, the instructions 216 are executable to control the display system 202 to project images at a selected frame rate. To avoid the aforementioned concerns of visible flicker in the images, a frame rate is selected such that the selected frame rate is equal to or greater than a CFF threshold 220. In some examples, the CFF threshold 220 is stored in the storage subsystem 214, for example, as a variable in firmware and/or within control register(s). This helps the CFF threshold 220 to be referenced and/or modified by the instructions 216 in various examples. In some examples, an initial value for the CFF threshold 220 can be stored, for example, after a reboot of the processor 218. Additionally, the instructions 216 are also executable to control a display luminance of the display system 202 by adjusting a modulation of light emitted from the left and/or right projectors 204, 206, as discussed with reference to FIG. 3.

In the example of FIG. 2, the instructions 216 control the display system 202 to project the images at a first frame rate 222. The instructions 216 are further executable to detect a change in a stimulus attribute of the images that modifies the CFF threshold 220. Examples of such changes are discussed with reference to FIGS. 5 to 9. In response, the instructions 216 adjust the selected frame rate of the display system 202 to project the images at a second frame rate 224. In examples where the detected change of the stimulus attribute decreases the CFF threshold 220, the second frame rate 224 is less than the first frame rate 222. For example, the second frame rate 224 can be in the range of 45 to 60 hertz, and the first frame rate 22 can be 90 hertz. Such a configuration helps to reduce compute and/or power consumption of the HMD device 200 than when the selected frame rate is increased. This helps with battery life of the HMD device 200, while also maintaining a flicker-free user experience.

Additionally, the instructions 216 can also be executable to receive an input indicating that the HMD device 200 has entered a power saving mode and in response, modulate a stimulus attribute of the images to decrease the CFF threshold 220. This enables the instructions 216 to also reduce the selected frame rate of the display system 202 in the power savings mode. Such a configuration can help to reduce power consumption on the HMD device 200. Further aspects of the processor 218 and the storage subsystem 214 are discussed with reference to FIG. 12.

Figure 3:
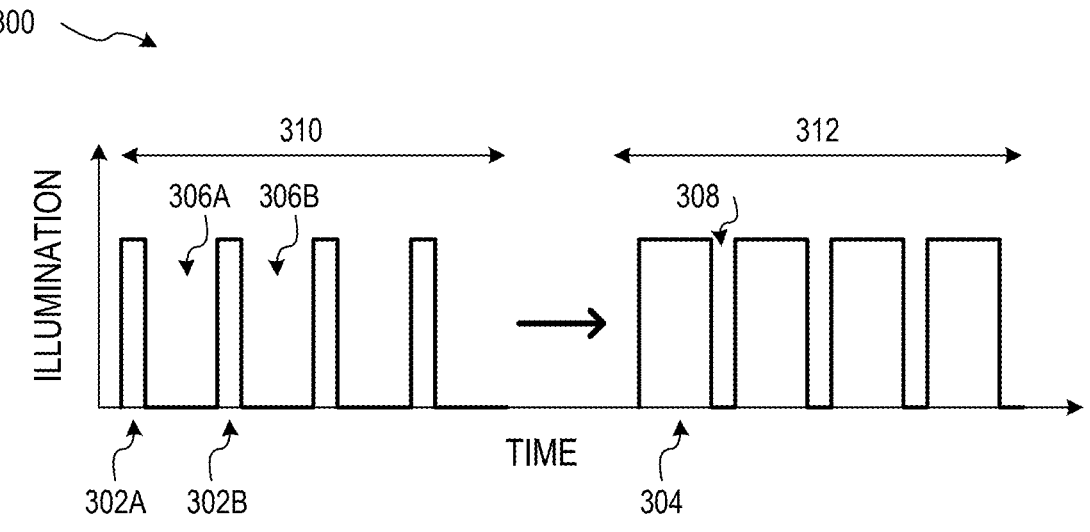
FIG. 3 shows an example timing diagram for display luminance.

As previously mentioned, display luminance of the display system 202 can be controlled by modulating the light emitted from the left and right projectors 204, 206. FIG. 3 depicts a timing diagram 300 illustrating example image frame display periods (302, 304) and corresponding inter-frame periods (306, 308). Briefly, the left projector 204 and the right projector 206 project image light during the image frame display periods (302, 304) and do not project the image light during the inter-frame periods (306, 308). As a specific example, the display system 202 projects a first image frame during a first image frame display period 302A and does not emit image light during a first inter-frame period 306A. Likewise, a second image frame is projected during a second image frame display period 302B, and so forth. The durations of the image frame display periods 302, 304 and the inter-frame periods 306, 308 can vary based, for example, upon a selected display luminance. As depicted, a first display luminance 310 has less time in the image frame display period 302 than in the inter-frame period 306 and therefore is a relatively lower display luminance. In the depicted example, the display luminance of the display system 202 is increased to a second display luminance 312. As can be seen, the second display luminance 312 has less time in the inter-frame period 308 than in the image frame display period 304. FIG. 3 is illustrative. In other examples, the display system 202 may utilize another timing diagram.

During the image frame display periods of the display system 202, light emitted from the projectors impinge photoreceptor cells in the eyes of the user. In response, a chemical reaction occurs in the impinged photoreceptor cells and results in a transduction process that sends visual information to the brain. This visual information can be interpreted by the user as sight/vision. Additionally, the chemical reaction has a duration before it can be activated again, such as a time it takes to relax back to a ground state, for example. Different photoreceptor cells have different energies for activation and/or different relaxation times.

Further, as will be discussed, different types of photorecep-tor cells have different relative light sensitivities and spatial densities in the human eye.

The human eye has two main types of photoreceptors, referred to as rods and cones. Rods have a high relative sensitivity to a photon and take relatively less energy to activate the chemical reaction for transduction. In this man-ner, the rods are primarily responsible for low-light or scotopic vision. Additionally, the rods have a relatively faster relaxation time than the cones. In contrast, the cones are responsible for color vision (photopic vision) and pro-vide the ability to see a wide range of colors and perceive relatively fine details. The cones take relatively more energy for activation and have a relatively slower relaxation time than the rods. In addition to scotopic vision and photopic vision, the human eye also has mesopic vision which utilizes various mixtures of rods and cones.

Figure 4A:
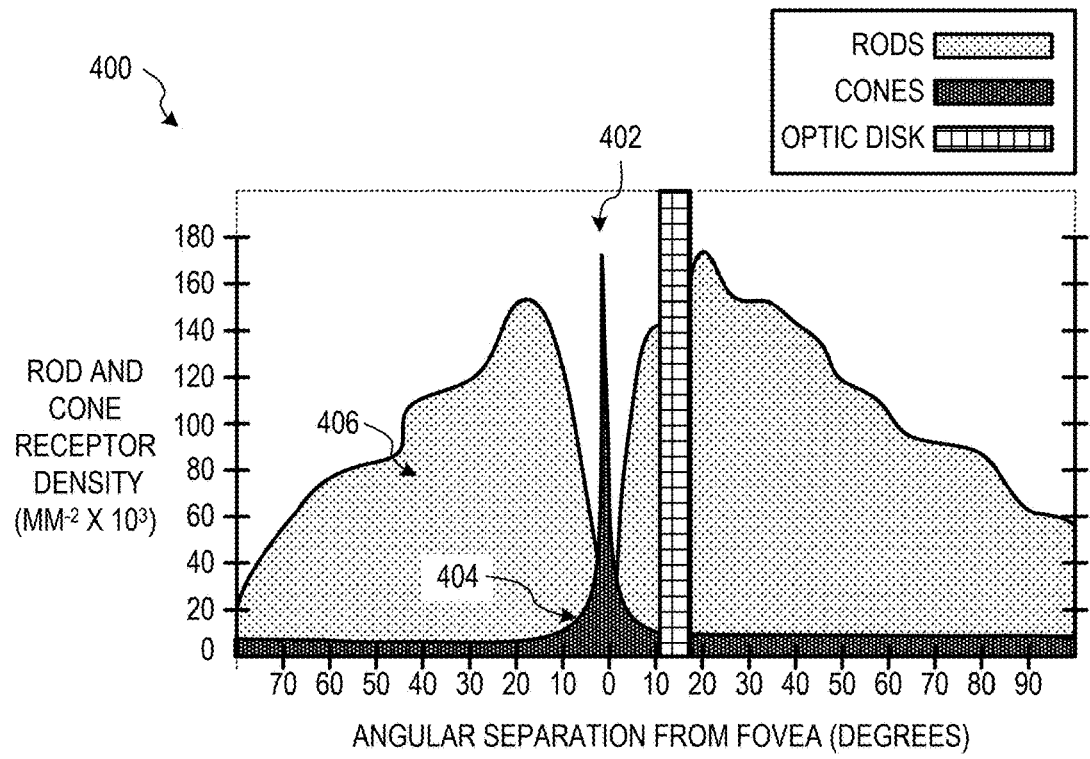
FIGS. 4A and 4B schematically depict example plots illustrating relative densities and light sensitivities, respectfully, for photoreceptor cells the human eye.

The rods and the cones vary in density in the human eye as a function of location on the retina in the human eye. FIG. 4A shows a graph 400 indicating example densities of rods and cones relative to angular separation from a fovea 402 of the human eye. The fovea 402 is generally located in a central region of the retina. As depicted in the graph 400, a cone density 404 peaks at zero degrees on the X-axis of the graph 400, which corresponds to the position of the fovea 402. The cone density 404 decreases rapidly moving angu-larly away from the position of the fovea 402 to about a constant level at around 10-15 degrees from the fovea 402. As can be seen, a rod density 406 peaks at approximately 20 degrees in angular separation from the fovea 402, which approximately corresponds to the angle where the cone density 404 reaches constant density. After peaking, the rod density 406 decreases non-linearly with increase angular separation from the fovea 402, as indicated by the slope of the rod density 406 shown in the graph 400. This region is referred to as the periphery region of the human eye and is associated with peripheral vision.

Figure 4B:
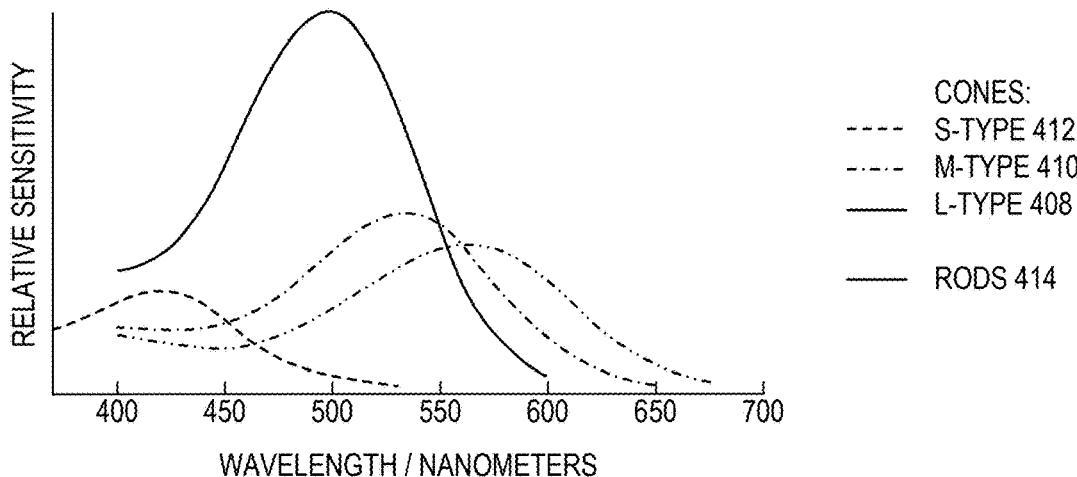

The cones can be categorized into three types that respond to different wavelength bands of light. FIG. 4B shows example plots illustrating relative light sensitivity as a function of wavelength for the different types of the cones. A majority of the cones in the human eye are L-type cones 408, which have a peak relative sensitivity in the red (long-wavelength) region. Additionally, around a third of the cones are M-type cones 410, which have a peak relative sensitivity in the green (mid-wavelength) region. Also, around 2% of the cones are S-type cones 412 with a peak relative sensitivity in the blue (short-wavelength) region. Collectively these cone types provide broadband sensitivity across the visible spectrum. In comparison, the rods 414 (solid line) have much greater relative sensitivity to short wavelengths than any of the cone types (408, 410, 412). As depicted, the peak relative sensitives for the different types of cones are in an order of a green color (highest), a red color, and a blue color (lowest). In FIG. 4B, the relative sensitivities are not necessarily represented to scale. FIGS. 4A and 4B are illustrative.

The physiological differences between the rods and the cones result in different responses to a change in a stimulus attribute of the impinging light. Thus, such changes can modify a CFF threshold. As discussed above, the HMD device 200 is configured to detect a change in the stimulus attribute of the project images that modifies the CFF thresh-old 220, and in response adjust the selected frame rate. FIGS. 5 to 9 schematically illustrate various examples of a change in a stimulus attribute that modifies the CFF thresh-old 220.

Figures 5A, 5B:
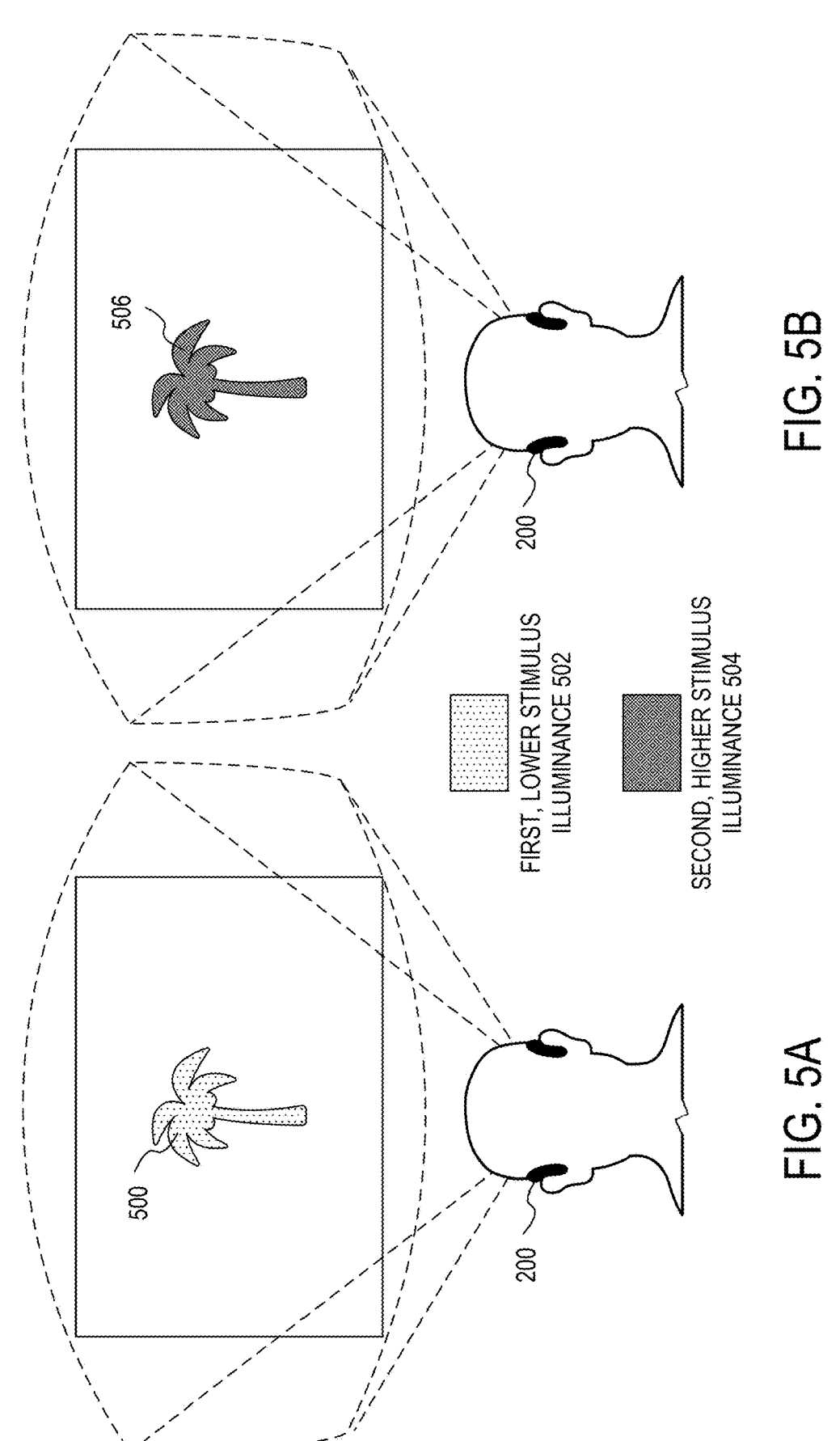
FIGS. 5A and 5B schematically illustrate an example change in a stimulus illuminance.

FIGS. 5A and 5B schematically depict a change in example stimulus illuminance. In FIG. 5A, the display system 202 is projecting a first image 500 (depicted here as a palm tree) at the first frame rate 222. As depicted, the first image 500 has a first, lower stimulus illuminance 502. In FIG. 5A, the first, lower stimulus illuminance 502 of the first image 500 activates more of the rods than the cones in the human eye. As previously discussed, the rods have a rela-tively higher sensitivity to light. Additionally, the first, lower stimulus illuminance 502 corresponds to a relatively shorter image frame display period of the display system 202 than a second, higher stimulus illuminance 504. In such a manner, the rods are likely to perceive flicker in the first image 500 at the first frame rate 222.

In contrast, a second image 506 having the second, higher stimulus illuminance 504, as depicted in FIG. 5B, is pre-dominantly perceived by the cones in the human eye. More specifically, to obtain the second, higher stimulus illumi-nance 504, the display system 202 projects light with a relatively longer image frame display period. As such, more photons are emitted during an image frame display period which activates more of the cones, which are relatively less sensitive to flicker than the rods. In such a manner, in response to detecting the change in stimulus illuminance from the first image 500 to the second image 506, the HMD device 200 can decrease the selected frame rate. The HMD device 200 can detect the change in the stimulus illuminance in any suitable manner. As one example, a stimulus illumi-nance can be determined based at least upon a display luminance, for example, by determining a display power and/or a duty cycle of the modulated light.

Figures 6A, 6B:
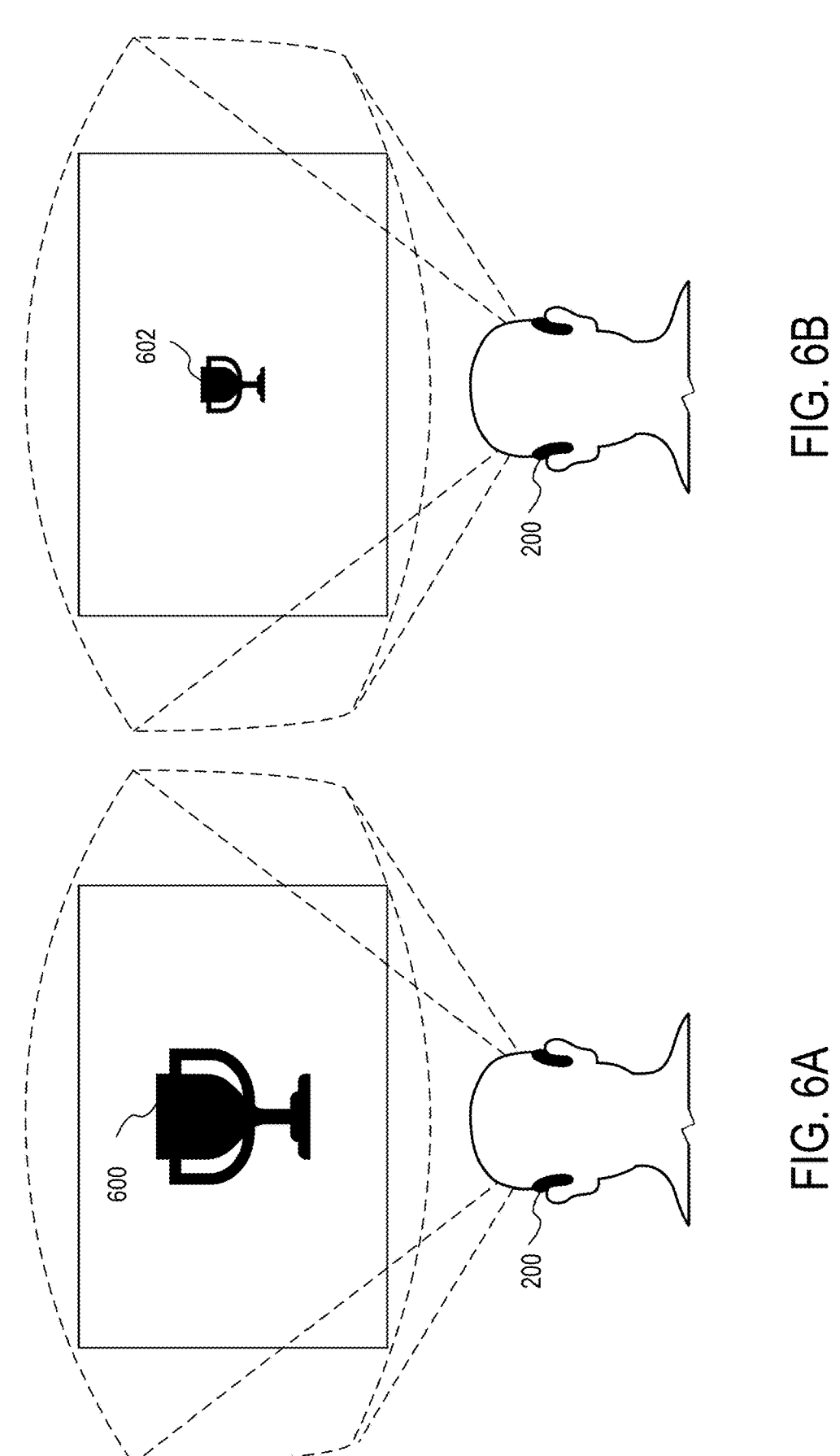
FIGS. 6A and 6B schematically illustrate an example change in a stimulus size.

In FIGS. 6A and 6B, the display system 202 is projecting another example first image 600 and second image 602 (depicted as trophy cups), respectively. As depicted, the first image 600 has a first stimulus size that is larger than a second stimulus size of the second image 602. The term "stimulus size" represents an apparent angular magnitude of an imaged object in a field of view of the user. Switching from the first image 600 to the second image 602 results in a change in the stimulus size that decreases the CFF thresh-old 220. More specifically, the second image 602 activates fewer rods and cones than the first image 600. The HMD device 200 can detect a change in the stimulus size in any suitable manner, for example, by analyzing content of the projected images. Such analysis can be performed at any suitable stage of the rendering pipeline and can include edge-detecting algorithms, geometrical analyses, suitable Fourier analyses, and/or suitable combinations thereof.

Figure 7:
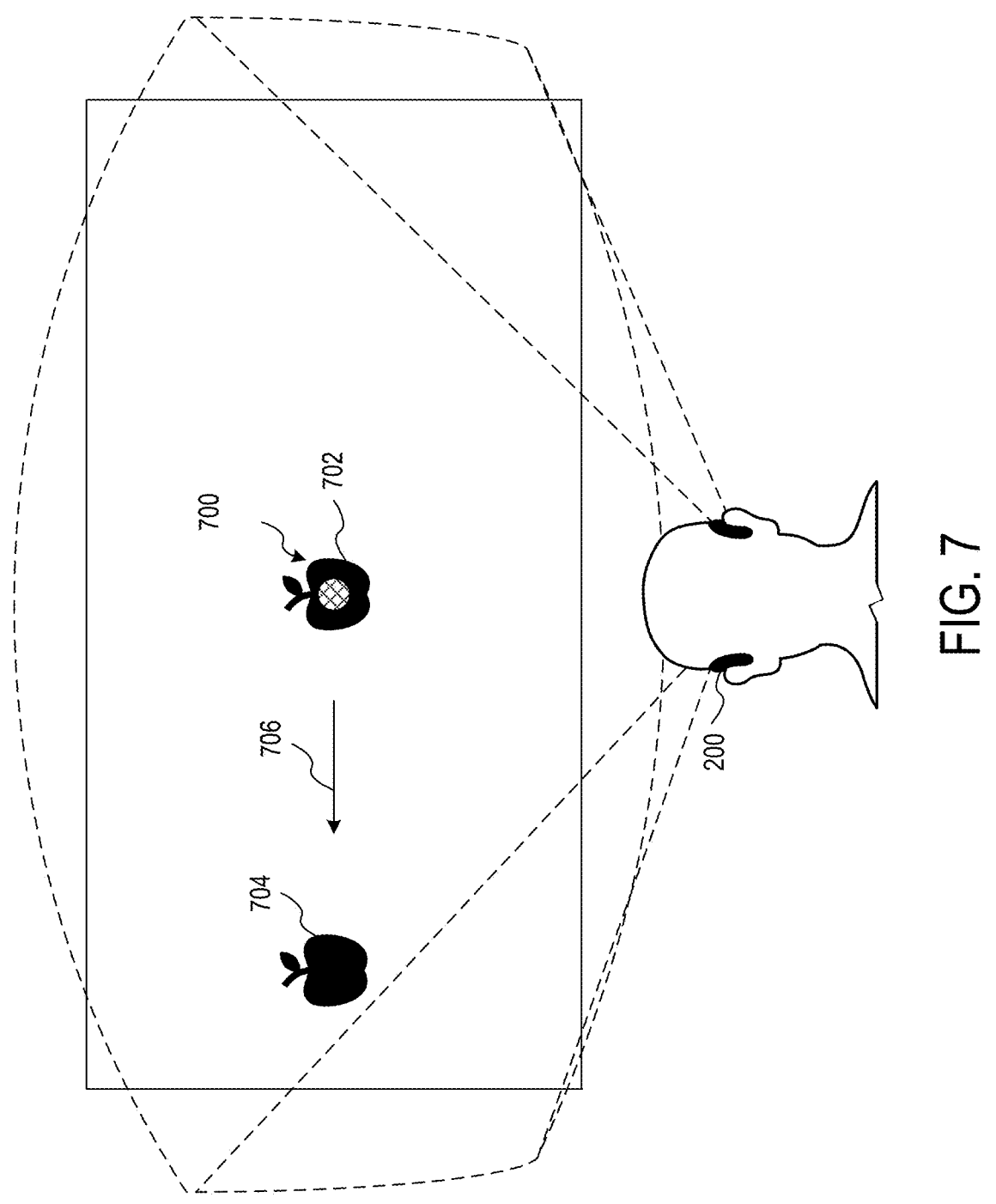
FIG. 7 schematically illustrates an example change in stimulus location.

FIG. 7 schematically illustrates a change in example stimulus location. Here, the user of the HMD device 200 is directing a gaze towards a point 700 (depicted in cross-hatch). As depicted, a first location 702 of an image (de-picted here as an apple) is at the location 700, and thus centrally located relative to the fovea 402. As such a first stimulus location of the image at the first location 702 has a relatively low eccentricity. In the depicted example, the image moves from the first location 702 to a second location 704, as indicated by 706. Here, the user maintains directing the gaze towards the location 700. As such, a second stimulus location of the image at the second location 704 has a relatively high eccentricity. This increase in eccentricity from the first stimulus location to the second stimulus location results in the image being perceived in the periph-ery region of the human eye, which has a relatively low density of rods, as previously discussed. In the depicted example, the HMD device 200 detects a change in the stimulus location of the image that decreases the CFF threshold 220. Generally, there is a positive correlation between an eccentricity of the stimulus location and the CFF threshold 220 (up to 55 degrees in angle separation form the fovea 402). FIG. 7 is illustrative.

Figures 8A, 8B:
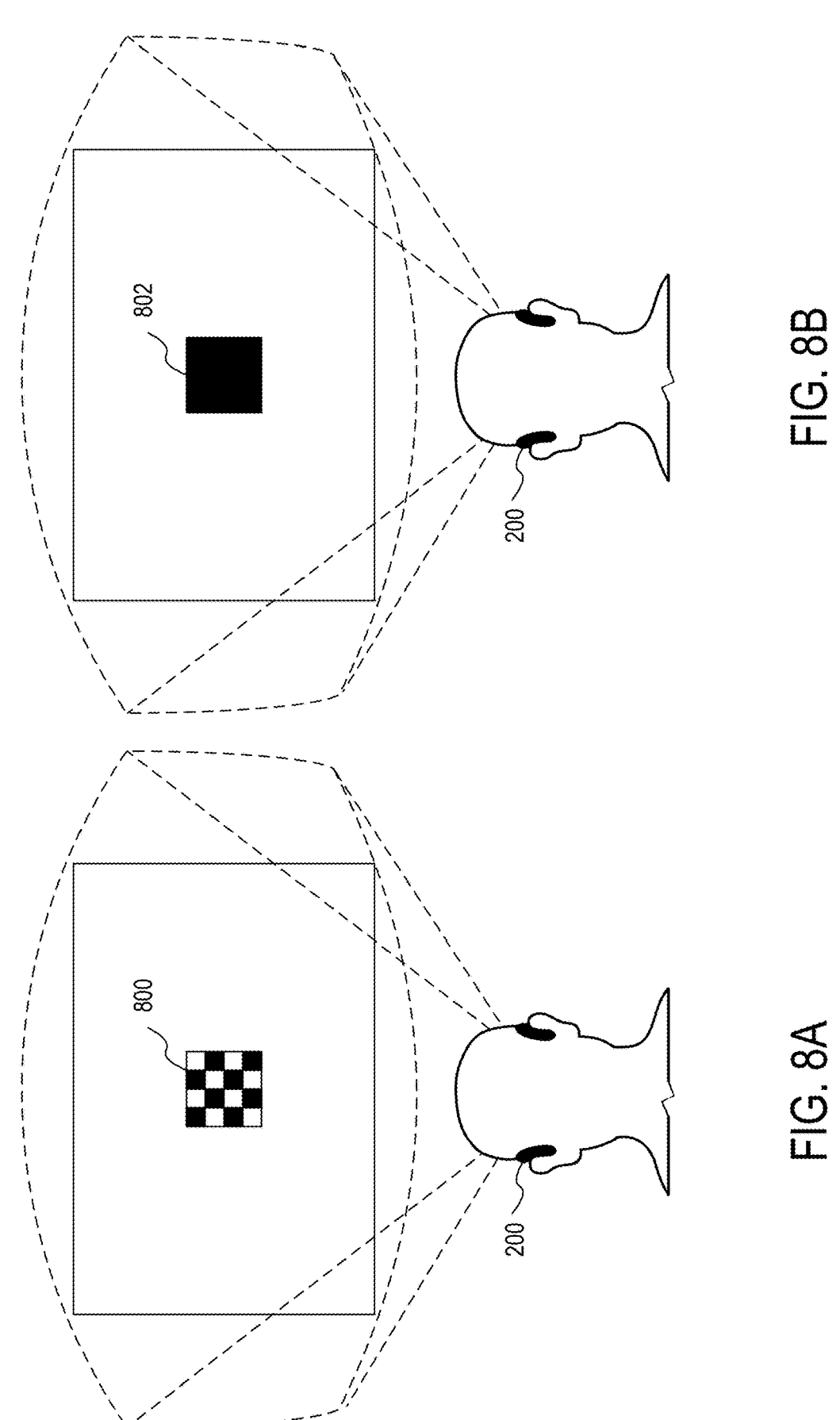
FIGS. 8A and 8B schematically illustrate an example change in stimulus spatial frequency.

Another stimulus attribute is a stimulus spatial frequency. In FIG. 8A, the HMD device 200 projects a first image 800 (depicted as a checkered-filled square). Here, the checked squares have a relatively fine detail with relatively sharp edges having relatively high contrast between adjacent squares. Therefore, the first image 800 has a relatively high stimulus spatial frequency, and likewise a higher CFF threshold. As depicted in FIG. 8B, a second image 802 comprises a solid square which has a lower stimulus spatial frequency than the first image 800. This decrease in the stimulus spatial frequency is sufficient to decrease the CFF threshold 220. The HMD device 200 can detect a change in the stimulus spatial frequency in any suitable manner. Example techniques for analyzing spatial frequency include Fourier analysis or other suitable special/frequency domain transform), pixel-by-pixel analysis, edge detection algorithms, and/or text detection algorithms.

Figures 9A, 9B, 9C:
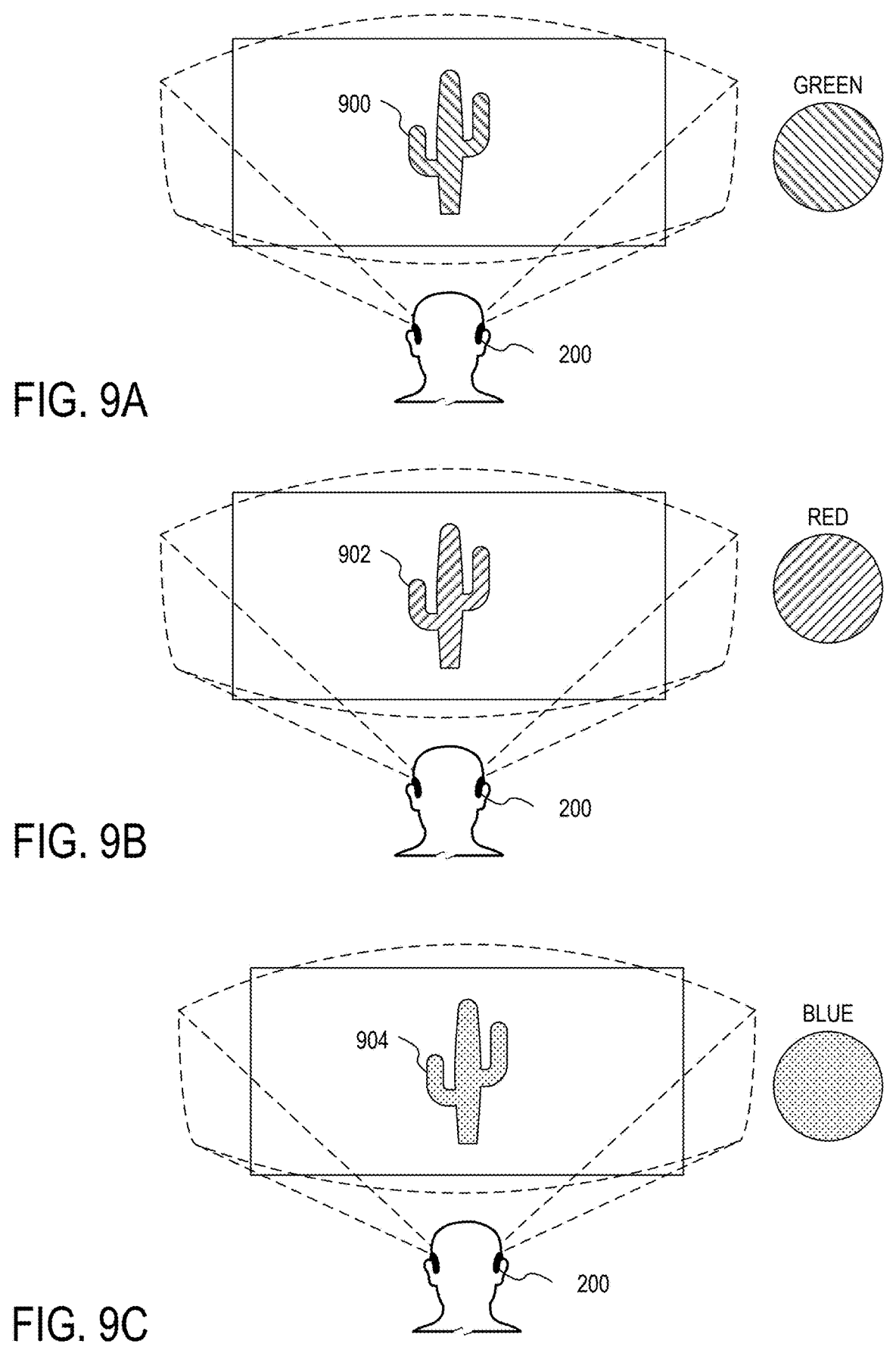

As previously mentioned, different cone types have peak relative sensitives in an order of a green color (highest), a red color, and a blue color (lowest). Likewise, the green-sensing cones (M-type) have a higher CFF threshold than the blue-sensing cones (S-type). FIGS. 9A, 9B, and 9C schematically illustrate an example series of monochromatic images, depicted as here cacti. In FIG. 9A, the HMD device 200 projects a first image 900 comprising the green color. In some examples, a stimulus color distribution of the green color, the red color, and the blue color of the first image 900 is a ratio of 1:0:0. In other examples, another suitable notation may be used to express a stimulus color distribution. The color of the first image 900 is modulated to the red color forming a second image 902, as depicted in FIG. 9B. The HMD device 200 detects the change in the stimulus color distribution from the first image 900 to the second image 902. As a specific example, the stimulus color distribution changed from 1:0:0 to 0:1:0 (the green color, the red color, the blue color). Additionally, the HMD device 200 can reduce the selected frame rate of the display system 202 based at least upon the detected change.

Next, the color of the second image 902 is further modulated from the red color to the blue color forming a third image 904, as depicted in FIG. 9C. Here, the HMD device 200 detects another change in the stimulus color distribution from 0:1:0 to 0:0:1 (the green color, the red color, the blue color). As previously discussed, the peak relative sensitivity of the blue-sensing cones is lower than the green-sensing cones and the red-sensing cones. Therefore, the HMD device 200 can further reduce the selected frame rate from that utilized in FIG. 9B with the second image 902. The HMD device 200 can detect a change in the stimulus color distribution of the images in any suitable manner. For example, the HMD device 200 may determine a spectral power distribution (SPD) of the images and/or a portion of the images to detect the change in the stimulus color distribution. While discussed with reference to monochromatic images, other images may have combinations of the green color, the red color, and/or the blue color in other examples. In such examples, the stimulus color distribution can be determined in any suitable manner to detect the change in the stimulus color distribution. In some such examples, a relative value of each color can be determined based at least upon a relative overall intensity of pixels in a specified color. In other such examples, a total amount of the specific color present in the image can be determined. FIGS. 9A, 9B, and 9C are illustrative.

While FIGS. 5 to 9 are discussed with reference to a change in a single stimulus attribute, in other examples, a projected image can have a plurality of stimulus attributes. In such examples, the HMD device 200 can detect changes in one or more stimulus attributes of the plurality of attributes. In some such examples, each of the plurality of stimulus attributes may have a different weighted priority. Additionally or alternatively, the HMD device 200 can modulate one stimulus attribute of the plurality of attributes to decrease the CFF threshold 220 (and likewise the selected frame rate) in response to an input indicating that the HMD device 200 has entered a power saving mode, as discussed with reference to FIG. 11.

FIG. 10 illustrates a flowchart of an example method 1000 for adjusting a frame rate in response to detecting a change in a stimulus attribute of projected images. The method 1000 can be performed on any suitable HMD device, such as the HMD device 100 and the HMD device 200, for example. The method 1000 comprises, at 1002, projecting images at a first frame rate using the display system. The first frame rate is selected to be above a CFF threshold of the human eye.

The method 1000 further includes detecting a change in a stimulus attribute of the images that modifies the CFF threshold, as indicated at 1004. The stimulus attribute can be any suitable stimulus attribute of the images including examples disclosed herein. In some examples, detecting the change in the stimulus attribute can comprise detecting a change in a stimulus illuminance that decreases the CFF threshold, as indicated at 1006. Alternatively or additionally, in some examples, detecting the change in the stimulus attribute can comprise, at 1008, detecting a change in a stimulus size that decreases the CFF threshold. Alternatively or additionally, at 1010, in some examples, detecting the change in the stimulus attribute can comprise detecting a change in a stimulus location that decreases the CFF threshold. Alternatively or additionally, in some examples, detecting the change in the stimulus attribute can comprise detecting a change in a stimulus spatial frequency that decreases the CFF threshold, as indicated at 1012.

In response to detecting the change in the stimulus attribute, the method 1000 further includes, at 1014, adjusting a frame rate of the display system to project the images at a second frame rate. In some examples, the detected change in the stimulus attribute decreases the CFF threshold. In such examples, adjusting the frame rate of the display system to project the images at the second frame rate comprises, at 1016, reducing the frame rate of the display system to the second frame rate. At 1018, adjusting the frame rate of the display system to project the images at the second frame rate can comprise adjusting the frame rate of the display system based at least upon a detected change in a stimulus color distribution of a green color, a red color, and a blue color in the images. In other examples, 1016 and/or 1018 may be omitted.

The above example discloses reducing the frame rate of the display system in response to detecting a change in a stimulus attribute that decreases the CFF threshold to reduce compute and/or power consumption on the HMD device. Alternatively or additionally, the HMD device can be configured to modulate a stimulus attribute of the projected images to decrease the CFF threshold and therefore, decrease the frame rate and likewise, the power consumption. FIG. 11 illustrates a flowchart of an example method 1100 for modulating a stimulus attribute of projected images that modifies a CFF threshold. The method 1100 can be performed on any suitable HMD device, such as the HMD device 100 and the HMD device 200, for example. The method 1100 comprises, at 1102, projecting images at a first frame rate using a display system of the display device. The first frame rate is selected to be higher than a CFF threshold of the human eye. At 1104, the method 1100 further comprises receiving an input indicating that the HMD device has entered a power saving mode. The input may originate from a processor, microcontroller, firmware, or combinations thereof on the HMD device. Alternatively or additionally, the input may be a user input.

In response, the method 1100 comprises, at 1106, modulating a stimulus attribute of the images to decrease the CFF threshold. In some examples, the stimulus attribute is one of a plurality of stimulus attributes of the images. In some such examples, one or more selected stimulus attributes may be modulated. At 1108, modulating the stimulus attribute to decrease the CFF threshold can comprise reducing one or more of a stimulus size or a stimulus spatial frequency. In some examples, modulating the stimulus attribute to decrease the CFF threshold can comprise increasing an eccentricity of a stimulus location of the images, as indicated at 1110.

The method 1100 further comprises reducing a frame rate of the display system to project the images at a second frame rate after modulating the stimulus attribute at 1112. In such a manner, the method 1100 helps to reduce compute and/or power consumption on the HMD device by modulating a stimulus attribute of the images to reduce the frame rate.

In some embodiments, the methods and processes described herein may be tied to a computing system of one or more computing devices. In particular, such methods and processes may be implemented as a computer-application program or service, an application-programming interface (API), a library, and/or other computer-program product.

Figure 12:
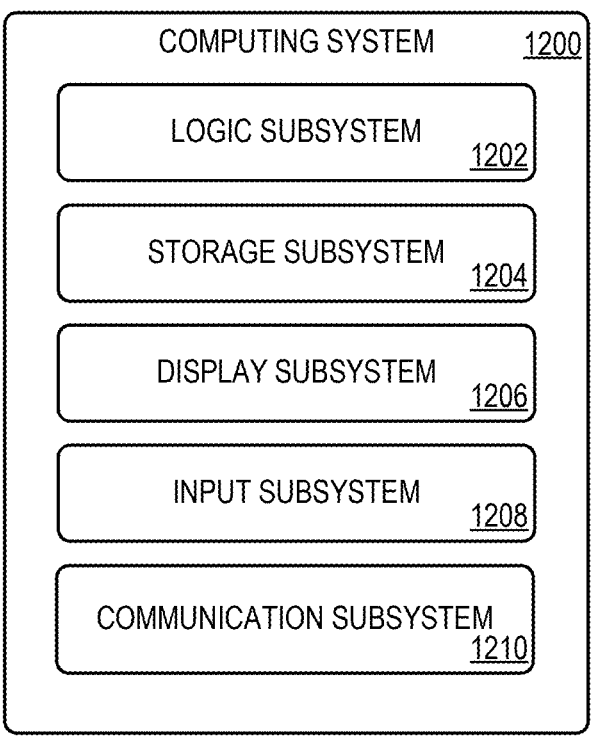
FIG. 12 shows a block diagram of an example computing system.

FIG. 12 schematically shows a non-limiting embodiment of a Computing system 1200 that can enact one or more of the methods and processes described above. Computing system 1200 is shown in simplified form. Computing system 1200 may take the form of one or more personal computers, server computers, tablet computers, home-entertainment computers, network computing devices, gaming devices, mobile computing devices, mobile communication devices (e.g., smart phone), and/or other computing devices. The HMD device 100 and the HMD device 200 are examples of the computing system 1200.

Computing system 1200 includes a logic subsystem 1202 and a storage subsystem 1204. Computing system 1200 may optionally include a display subsystem 1206, input subsystem 1208, communication subsystem 1210, and/or other components not shown in FIG. 12.

Logic subsystem 1202 includes one or more physical devices configured to execute instructions. For example, the logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result. For example, the logic subsystem 1202 can execute the instructions 216.

The logic machine may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of the logic machine optionally may be distributed among two or more separate devices, which may be remotely located and/or configured for coordinated processing. Aspects of the logic machine may be virtualized and executed by remotely accessible, networked computing devices configured in a cloud-computing configuration.

Storage subsystem 1204 includes one or more physical devices configured to hold instructions executable by the logic machine to implement the methods and processes described herein, such as the method 1000 and the method 1100, for example. When such methods and processes are implemented, the state of storage subsystem 1204 may be transformed—e.g., to hold different data.

Storage subsystem 1204 may include removable and/or built-in devices. Storage subsystem 1204 may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage subsystem 1204 may include volatile, nonvolatile, dynamic, static, read/write, read-only, random-access, sequential-access, location-addressable, file-addressable, and/or content-addressable devices.

It will be appreciated that storage subsystem 1204 includes one or more physical devices. However, aspects of the instructions described herein alternatively may be propagated by a communication medium (e.g., an electromagnetic signal, an optical signal, etc.) that is not held by a physical device for a finite duration.

Aspects of logic subsystem 1202 and storage subsystem 1204 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module," "program," and "engine" may be used to describe an aspect of Computing system 1200 implemented to perform a particular function. In some cases, a module, program, or engine may be instantiated via logic subsystem 1202 executing instructions held by storage subsystem 1204. It will be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" may encompass individual or groups of executable files, data files, libraries, drivers, scripts, database records, etc.

When included, display subsystem 1206 may be used to present a visual representation of data held by storage subsystem 1204. This visual representation may take the form of a graphical user interface (GUI). As the herein described methods and processes change the data held by the storage machine, and thus transform the state of the storage machine, the state of display subsystem 1206 may likewise be transformed to visually represent changes in the underlying data. Display subsystem 1206 may include one or more display devices utilizing virtually any type of technology. Such display devices may be combined with logic subsystem 1202 and/or storage subsystem 1204 in a shared enclosure, or such display devices may be peripheral display devices.

When included, input subsystem 1208 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

When included, communication subsystem 1210 may be configured to communicatively couple Computing system 1200 with one or more other computing devices. Communication subsystem 1210 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow Computing system 1200 to send and/or receive messages to and/or from other devices via a network such as the Internet.

One example provides a head-mounted display (HMD) device comprising a display system, a logic subsystem, and a storage subsystem comprising instructions executable by the logic subsystem. The instructions are executable to project images at a first frame rate using the display system, detect a change in a stimulus attribute of the images that modifies a critical flicker fusion (CFF) threshold of a human eye, and in response, adjust a frame rate of the display system to project the images at a second frame rate. In some such examples, the instructions executable to adjust the frame rate of the display system to project the images at the second frame rate alternatively or additionally comprise instructions executable to reduce the frame rate of the display system to the second frame rate. In some such examples, the instructions executable to detect the change in the stimulus attribute alternatively or additionally comprise instructions executable to detect a change in a stimulus illuminance that decreases the CFF threshold. In some such examples, the instructions executable to detect the change in the stimulus attribute alternatively or additionally comprise instructions executable to detect a change in a stimulus size that decreases the CFF threshold. In some such examples, the instructions executable to detect the change in the stimulus attribute alternatively or additionally comprise instructions executable to detect a change in a stimulus location that decreases the CFF threshold. In some such examples, the instructions executable to detect the change in the stimulus attribute alternatively or additionally comprise instructions executable to detect a change in a stimulus spatial frequency that decreases the CFF threshold. In some such examples, the instructions executable to adjust the frame rate of the display system to project the images at the second frame rate alternatively or additionally comprise instructions executable to adjust the frame rate of the display system based at least upon a detected change in a stimulus color distribution of green color, red color, and blue color in the images. In some such examples, the stimulus attribute alternatively or additionally is one of a plurality of stimulus attributes of the images, and the instructions are alternatively or additionally executable to receive an input indicating that the HMD device has entered a power saving mode, and in response, modulate a selected stimulus attribute of the plurality of stimulus attributes of the images to decrease the CFF threshold.

Another example provides a method on a head-mounted display (HMD) device comprising a display system. The method comprises projecting images at a first frame rate using the display system, detecting a change in a stimulus attribute of the images that modifies a critical flicker fusion (CFF) threshold of a human eye, and in response, adjusting a frame rate of the display system to project the images at a second frame rate. In some such examples, adjusting the frame rate of the display system to project the images at the second frame rate alternatively or additionally comprises reducing the frame rate of the display system to the second frame rate. In some such examples, detecting the change in the stimulus attribute alternatively or additionally comprises detecting a change in a stimulus illuminance that decreases the CFF threshold. In some such examples, detecting the change in the stimulus attribute alternatively or additionally comprises detecting a change in a stimulus size that decreases the CFF threshold. In some such examples, detecting the change in the stimulus attribute alternatively or additionally comprises detecting a change in a stimulus location that decreases the CFF threshold. In some such examples, detecting the change in the stimulus attribute alternatively or additionally comprises detecting a change in a stimulus spatial frequency that decreases the CFF threshold. In some such examples, adjusting the frame rate of the display system to project the images at the second frame rate alternatively or additionally comprises adjusting the frame rate of the display system based at least upon a detected change in a stimulus color distribution of green color, red color, and blue color in the images. In some such examples, the stimulus attribute alternatively or additionally is one of a plurality of stimulus attributes of the images, and the method alternatively or additionally comprises receiving an input indicating that the HMD device has entered a power saving mode, and in response, modulating a selected stimulus attribute of the plurality of stimulus attributes of the images to decrease the CFF threshold.

Another example provides a head-mounted display (HMD) device comprising a display system, a logic subsystem, and a storage subsystem comprising instructions executable by the logic subsystem. The instructions are executable to project images at a first frame rate using the display system, receive an input indicating that the HMD device has entered a power saving mode, and in response, modulate a stimulus attribute of the images to decrease a critical flicker fusion (CFF) threshold of a human eye. In some such examples, the instructions are alternatively or additionally executable to reduce a frame rate of the display system to project the images at a second frame rate after modulating the stimulus attribute. In some such examples, the instructions executable to modulate the stimulus attribute to decrease the CFF threshold alternatively or additionally comprise instructions executable to reduce one or more of a stimulus size or a stimulus spatial frequency. In some such examples, the instructions executable to modulate the stimulus attribute to decrease the CFF threshold alternatively or additionally comprise instructions executable to increase an eccentricity of a stimulus location.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A head-mounted display (HMD) device comprising:
a display system;
a logic subsystem; and
a storage subsystem comprising instructions executable by the logic subsystem to
    project images at a first frame rate using the display system,
    detect a change in a stimulus attribute of the images that modifies a critical flicker fusion (CFF) threshold of a human eye, the stimulus attribute being a characteristic of the images that is discernable by the human eye, wherein the stimulus attribute is one of a plurality of stimulus attributes,
    in response, adjust a frame rate of the display system to project the images at a second frame rate,
    receive an input indicating that the HMD device has entered a power saving mode, and
    in response, modulate a selected stimulus attribute of the plurality of stimulus attributes of the images to decrease the CFF threshold.

2. The HMD device of claim 1, wherein the instructions executable to adjust the frame rate of the display system to project the images at the second frame rate comprise instructions executable to reduce the frame rate of the display system to the second frame rate.

3. The HMD device of claim 2, wherein the instructions executable to detect the change in the stimulus attribute comprise instructions executable to detect a change in a stimulus illuminance that decreases the CFF threshold.

4. The HMD device of claim 2, wherein the instructions executable to detect the change in the stimulus attribute comprise instructions executable to detect a change in a stimulus size that decreases the CFF threshold.

5. The HMD device of claim 2, wherein the instructions executable to detect the change in the stimulus attribute comprise instructions executable to detect a change in a stimulus location that decreases the CFF threshold.

6. The HMD device of claim 2, wherein the instructions executable to detect the change in the stimulus attribute comprise instructions executable to detect a change in a stimulus spatial frequency that decreases the CFF threshold.

7. The HMD device of claim 1, wherein the instructions executable to adjust the frame rate of the display system to project the images at the second frame rate comprise instructions executable to adjust the frame rate of the display system based at least upon a detected change in a stimulus color distribution of green color, red color, and blue color in the images.

8. On a head-mounted display (HMD) device comprising a display system, a method comprising:

projecting images at a first frame rate using the display system,
    detecting a change in a stimulus attribute of the images that modifies a critical flicker fusion (CFF) threshold of a human eye, the stimulus attribute being a characteristic of the images that is discernable by the human eye, wherein the stimulus attribute is one of a plurality of stimulus attributes,
    in response, adjusting a frame rate of the display system to project the images at a second frame rate,
    receiving an input indicating that the HMD device has entered a power saving mode, and
    in response, modulating a selected stimulus attribute of the plurality of stimulus attributes of the images to decrease the CFF threshold.

9. The method of claim 8, wherein adjusting the frame rate of the display system to project the images at the second frame rate comprises reducing the frame rate of the display system to the second frame rate.

10. The method of claim 9, wherein detecting the change in the stimulus attribute comprises detecting a change in a stimulus illuminance that decreases the CFF threshold.

11. The method of claim 9, wherein detecting the change in the stimulus attribute comprises detecting a change in a stimulus size that decreases the CFF threshold.

12. The method of claim 9, wherein detecting the change in the stimulus attribute comprises detecting a change in a stimulus location that decreases the CFF threshold.

13. The method of claim 9, wherein detecting the change in the stimulus attribute comprises detecting a change in a stimulus spatial frequency that decreases the CFF threshold.

14. The method of claim 8, wherein adjusting the frame rate of the display system to project the images at the second frame rate comprises adjusting the frame rate of the display system based at least upon a detected change in a stimulus color distribution of green color, red color, and blue color in the images.

15. A head-mounted display (HMD) device comprising:
a display system;
a logic subsystem; and
a storage subsystem comprising instructions executable by the logic subsystem to
    project images at a first frame rate using the display system,
    receive an input indicating that the HMD device has entered a power saving mode,
    in response, modulate a stimulus attribute of the images to decrease a critical flicker fusion (CFF) threshold of a human eye, the stimulus attribute being a characteristic of the images that is discernable by the human eye, and
    reduce a frame rate of the display system to project the images at a second frame rate after modulating the stimulus attribute.

16. The HMD device of claim 15, wherein the instructions executable to modulate the stimulus attribute to decrease the CFF threshold comprise instructions executable to reduce one or more of a stimulus size or a stimulus spatial frequency.

17. The HMD device of claim 15, wherein the instructions executable to modulate the stimulus attribute to decrease the CFF threshold comprise instructions executable to increase an eccentricity of a stimulus location.

* * * * *